(12) United States Patent
Yeh et al.

(10) Patent No.: US 8,708,976 B1
(45) Date of Patent: Apr. 29, 2014

(54) NEEDLELESS CONNECTOR WITH A TORTUOUS FLUID FLOW PATH

(71) Applicants: Jonathan Yeh, Diamond Bar, CA (US); Christopher J. Zollinger, Chino Hills, CA (US); Tyler Devin Panian, Long Beach, CA (US)

(72) Inventors: Jonathan Yeh, Diamond Bar, CA (US); Christopher J. Zollinger, Chino Hills, CA (US); Tyler Devin Panian, Long Beach, CA (US)

(73) Assignee: Carefusion 303, Inc., San Diego, CA (US)

( * ) Notice: Subject to any disclaimer, the term of this patent is extended or adjusted under 35 U.S.C. 154(b) by 0 days.

(21) Appl. No.: 13/829,219

(22) Filed: Mar. 14, 2013

(51) Int. Cl.
*A61M 5/14* (2006.01)

(52) U.S. Cl.
USPC .......................................... 604/256; 604/236

(58) Field of Classification Search
USPC .................................. 604/256, 236
See application file for complete search history.

(56) References Cited

U.S. PATENT DOCUMENTS

| | | | | |
|---|---|---|---|---|
| 7,520,489 | B2* | 4/2009 | Ruschke et al. | 251/149.7 |
| 2004/0238050 | A1* | 12/2004 | Hamblin et al. | 137/625.37 |
| 2006/0163515 | A1* | 7/2006 | Ruschke | 251/149.7 |
| 2010/0059702 | A1* | 3/2010 | Mansour et al. | 251/331 |
| 2012/0310179 | A1* | 12/2012 | Truitt et al. | 604/249 |
| 2012/0316514 | A1* | 12/2012 | Mansour | 604/256 |
| 2013/0030386 | A1* | 1/2013 | Panian et al. | 604/256 |

* cited by examiner

*Primary Examiner* — Nicholas Lucchesi
*Assistant Examiner* — Gerald Landry, II
(74) *Attorney, Agent, or Firm* — McDermott Will & Emery LLP

(57) ABSTRACT

A needleless connector has a housing with an internal cavity having an interior surface, a port, an output flow channel, and a fluid flow path through the cavity between the port and the output flow channel. A collapsible valve is disposed within the cavity. The valve has one or more rings each having a surface that is in sealing contact with the interior surface of the housing. There are one or more notches formed in each of the one or more rings, and the flow path passes through one of the notches in each of the one or more rings.

17 Claims, 5 Drawing Sheets

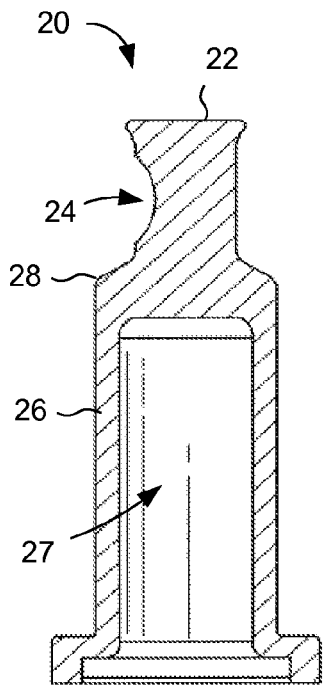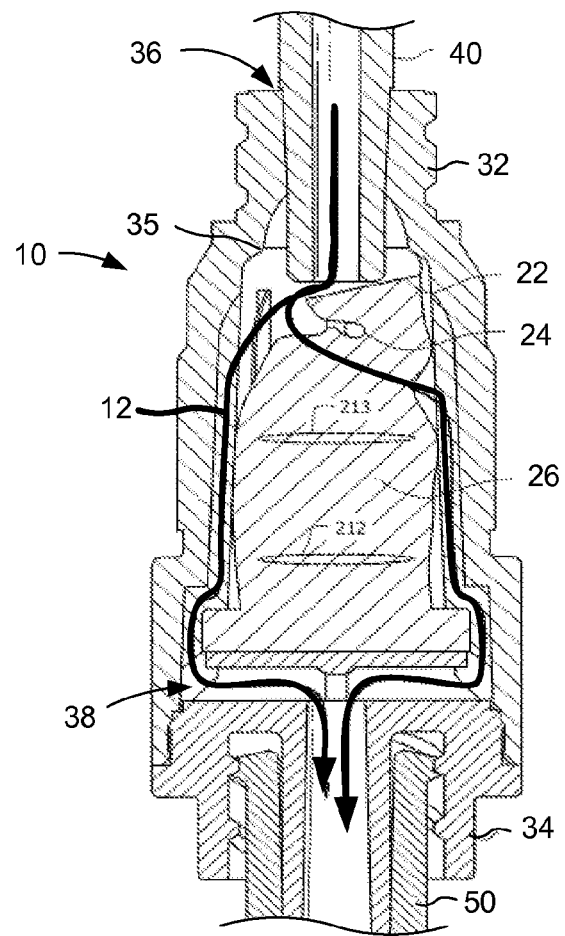
FIG. 1A
PRIOR ART
FIG. 1B
PRIOR ART

NEEDLELESS CONNECTOR WITH A TORTUOUS FLUID FLOW PATH

CROSS-REFERENCES TO RELATED APPLICATIONS

Not applicable.

BACKGROUND

1. Field

The present disclosure generally relates to needleless connectors, and, in particular, to connectors with a tortuous fluid flow path.

2. Description of the Related Art

Medical treatments often include the infusion of a medical fluid, for example a saline solution or a liquid medication, to patients using an intravenous (IV) catheter that is connected though an arrangement of flexible tubing and fittings, commonly referred to as an "IV set," to a source of fluid, for example an IV bag. The fittings commonly include interconnectable male and female needleless connectors having a "Luer taper" conforming to an International Standards Organization (ISO) standard. Certain connectors have a self-sealing feature to prevent leakage of fluid from the attached tubing when the connector is decoupled from a mating connector.

One conventional needleless connector 10, shown in FIGS. 1A-1B, has a collapsible internal valve 20 made of a flexible material. When a force is applied to the top 22 of the valve 20 by the tip of a male Luer fitting 40, the valve 20 folds at a "smiley cut" 24 located in an upper portion of the valve 20, thereby opening a flow path 12 through the connector 10. The flow path 12 is generally linear between the cylindrical body 26 of the valve 20 and the body 32 and then through the base 34 into a mated female Luer fitting 50. This flow path 12 may not flush certain regions within the fluid-filled space within connector 10. As some medical fluids degrade with time, this non-flushed portion of the fluid may present a hazard to a patient.

SUMMARY

The self-sealing needleless female Luer connector disclosed herein provides a tortuous path through the connector such that fluid flowing through the connector flushes the entire path, thereby reducing the non-flushed portion of the fluid-filled volume within the connector.

In certain embodiments, a needleless connector is disclosed that includes a housing having an internal cavity with an interior surface, a port, an output flow channel, and a fluid flow path through the cavity between the port and the output flow channel. The connector also includes a collapsible valve disposed within the cavity. The valve has one or more rings each having a respective surface in sealing contact with the interior surface of the housing, with one or more notches formed in each of the one or more rings. The flow path passes through one of the one or more notches in each respective one of the one or more rings.

BRIEF DESCRIPTION OF THE DRAWINGS

The accompanying drawings, which are included to provide further understanding and are incorporated in and constitute a part of this specification, illustrate disclosed embodiments and together with the description serve to explain the principles of the disclosed embodiments. In the drawings:

FIGS. 1A-1B are cross-sections of a conventional needleless connector.

DETAILED DESCRIPTION

Figures 2A, 2B:
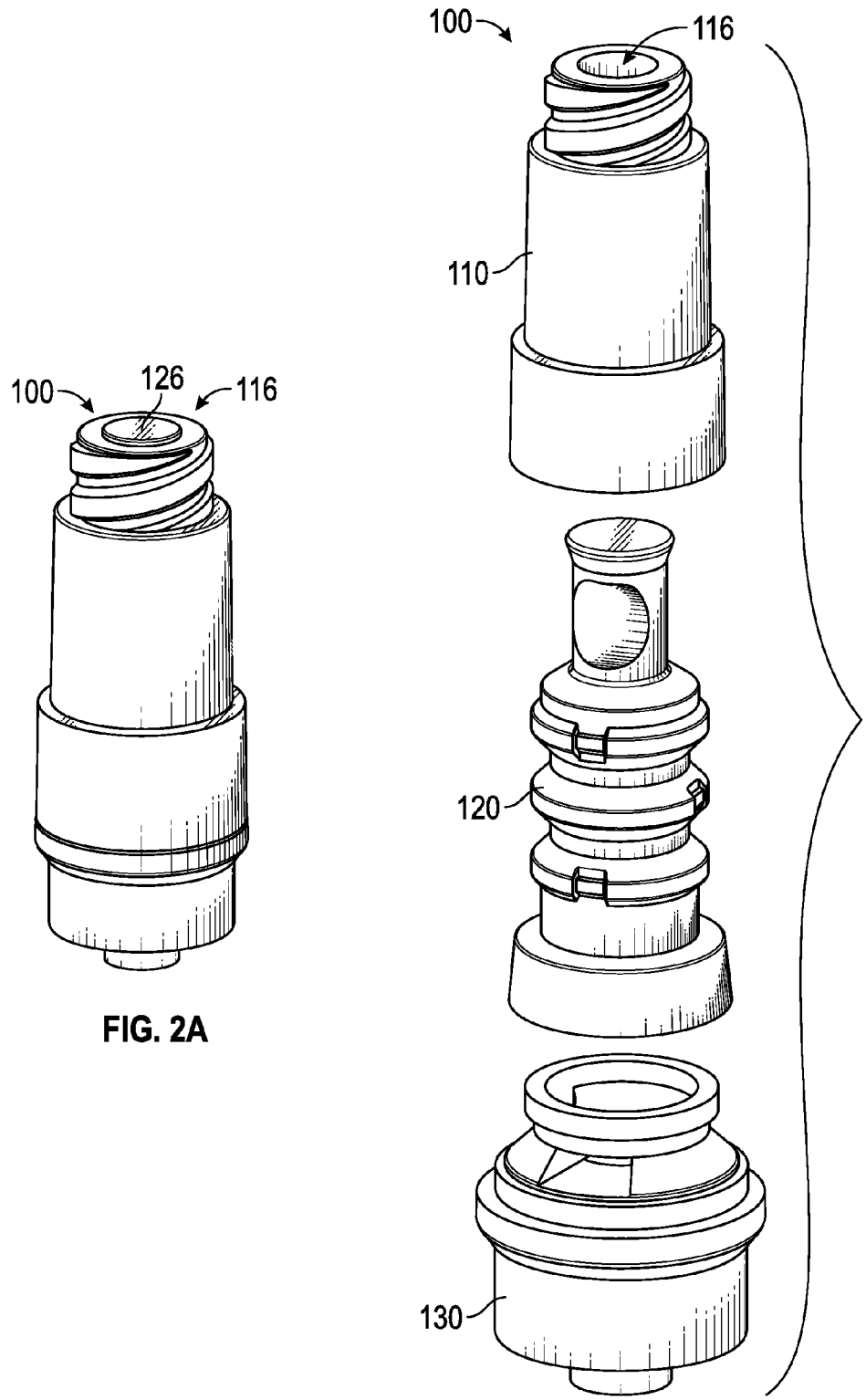
FIGS. 2A-2C are perspective views of an exemplary needleless connector according to certain aspects of the present disclosure.

It is advantageous to provide a self-sealing, needleless connector that accepts male Luer fittings that meet the ISO standard and has an internal flow path that reduces, compared to conventional connectors, the portion of the fluid-filled volume that is not flushed by fluid flowing through the disclosed connector.

In the following detailed description, numerous specific details are set forth to provide a full understanding of the present disclosure. It will be apparent, however, to one ordinarily skilled in the art that embodiments of the present disclosure may be practiced without some of the specific details. In other instances, well-known structures and techniques have not been shown in detail so as not to obscure the disclosure. In the referenced drawings, like numbered elements are the same or essentially similar. Reference numbers may have letter suffixes appended to indicate separate instances of a common element while being referred to generically by the same number without a suffix letter.

FIGS. 1A-1B are cross-sections of a conventional needleless connector 10. FIG. 1A depicts a collapsible valve 20 that is disposed in the housing top 32 of the connector 10, as shown in FIG. 1B. The valve 20 has a solid head with a "smiley cut" 24 formed on one side and a top surface 22. The valve has a cylindrical body 26 with a hollow interior 27. There is a shoulder 28 above the cylindrical portion 26.

FIG. 1B depicts the connector 10 in the activated position, i.e. a male Luer fitting 40 sealingly coupled to the connector 10 at port 36. The tip of the male Luer fitting 40 has displaced the external surface 22 downward and the applied force has caused the upper portion of the valve 20 to buckle toward the smiley cut 24 as well as causing the cylindrical wall 26 to buckle. In the activated configuration, the primary seal between the shoulder 28 and ridge 35 of the housing top 32, which are in contact when the connector 10 is in an unactuated position, is opened such that fluid may flow through the connector 10, as indicated by the fluid flow path 12 that passes from the male Luer fitting 40 between the top housing 32 and the valve 20 and then through channels 38 in the base 34 and out through a connected female Luer fitting 50. A needleless connector similar to the connector 10 described herein is described in detail in U.S. patent application Ser. No. 12/512,719, the entirety of which is hereby incorporated by reference.

While the conventional needleless connector 10 of FIGS. 1A-1B allows the connection and disconnection of a male Luer fitting and seals the flow path 12 when there is no fitting mated with the connector 10, it is generally desirable to have the fluid-filled space within the connector 10 fully flushed as fluid flows through the connector 10. With a generally linear flow path, as indicated by the example flow path 12, certain portions of the fluid-filled volume of connector 10 may not be flushed, which may result in some medication remaining the connector for an extended period of time. As medications may degrade over time, it is desirable to fully flush the fluid-filled volume within a needleless connector.

Figure 2C:
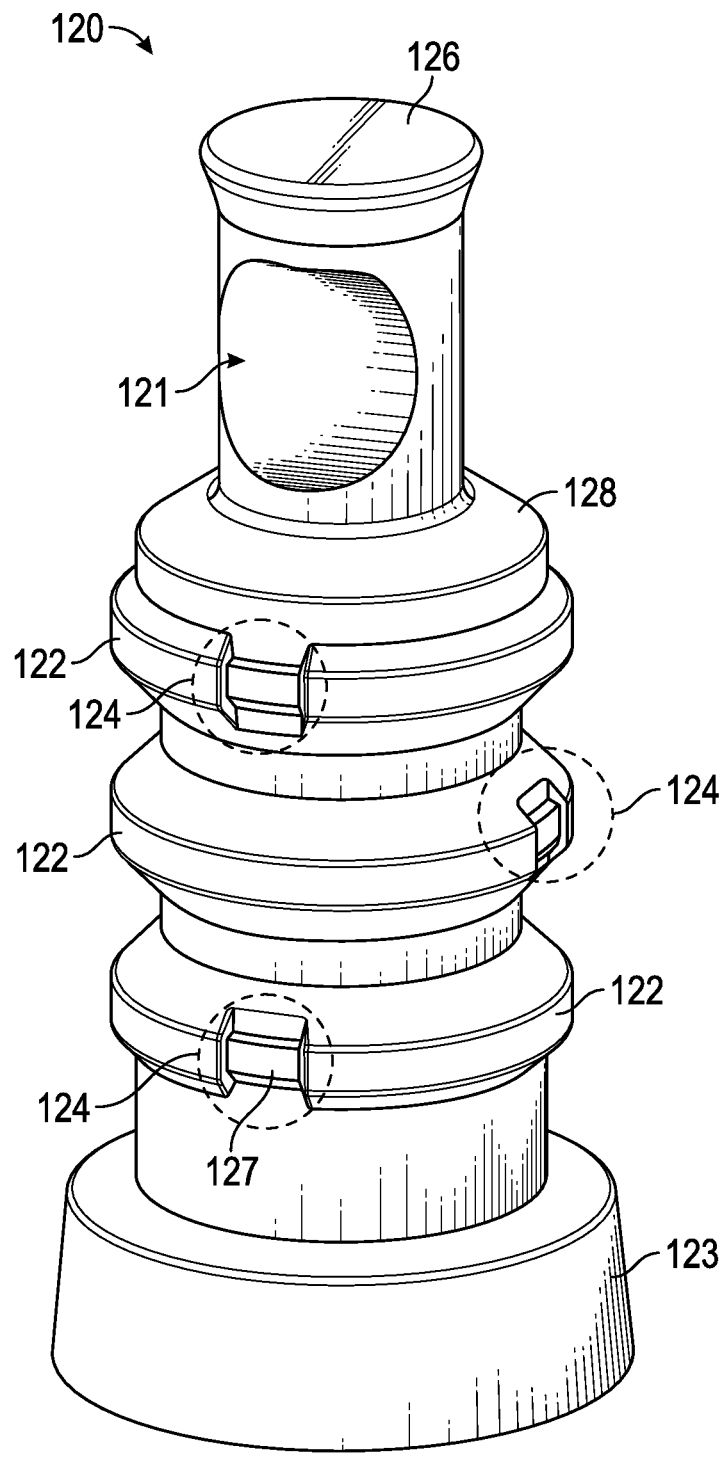

FIGS. 2A-2C are perspective views of an exemplary needleless connector 100 according to certain aspects of the present disclosure. FIG. 2A is a perspective view of an assembled connector 100, showing how the unbroken top surface 126 of a collapsible valve 120 blocks the port 116 and presents a smooth surface that can easily be disinfected prior to use.

FIG. 2B is an exploded view of the connector 100, showing how the collapsible valve 120 is captured between a lower housing 130 and an upper housing 110.

FIG. 2C is an enlarged view of the internal valve 120, showing a smiley cut 121 and a shoulder 128 that function in a manner similar to the smiley cut 24 and shoulder 28 of the conventional connector 10. The exemplary collapsible valve 120 has, in this embodiment, three sealing rings 122 disposed between the shoulder 128 and base 123. Each ring 122 has a cylindrical outer surface that is interrupted at one or more locations by a notch 124 that passes vertically through the respective ring 122. Each ring 122 has at least one notch 124, with the notches 124 of adjoining rings 122 offset circumferentially from each other. In certain embodiments, there are two notches 124 in each ring 122, with the two notches circumferentially disposed 180° from each other. In certain embodiments, the at least one notch 124 of a first ring is circumferentially disposed 90° from the notch 124 of a second ring 122 that is adjacent to the first ring 122. In certain embodiments, the notches 124 may be formed as simple interruptions of the ring 122 while, in other embodiments, the notches 124 may incorporate features such as ribs, bumps, or tapered surfaces, such as the bump 127 shown in FIG. 2C.

Figure 3:
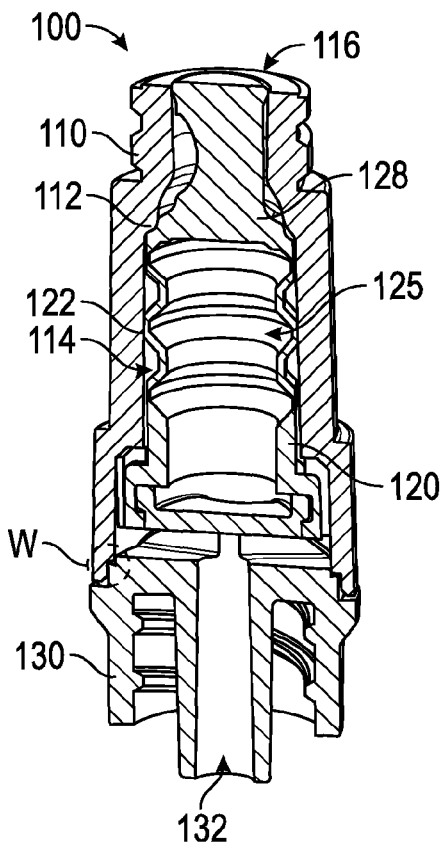
FIG. 3 is a cross-section of the exemplary valve in an unactuated position according to certain aspects of the present disclosure.

FIG. 3 is a cross-section of the exemplary valve 100 in an unactuated position according to certain aspects of the present disclosure. The shoulder 128 is in contact with a ridge 112 of the upper housing 110, thereby forming a primary seal that blocks flow through the connector 100. The lower housing 130 has an output flow path 132. The lower housing 130 and upper housing 110 are, in this example, ultrasonically welded to each other at location "W." In certain embodiments, the upper and lower housings 110, 130 may be sealingly joined using any method known to those of skill in the art, including bonding, solvent welding, spin welding, etc. The cylindrical surfaces of the rings 122 are in sealing contact with a cylindrical interior surface 114 of the upper housing 110. In this cross-sectional view, it can be seen that the valve 120 is hollow and the interior surface follows the contours of the rings 122, thereby forming a bellows 125 under each ring 122.

Figure 4A:
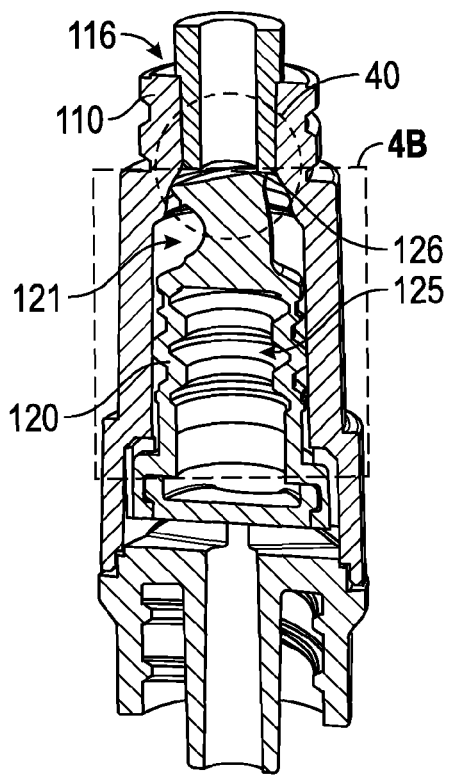
FIGS. 4A-4B are cross-sections of the exemplary valve in an actuated position according to certain aspects of the present disclosure.
Figure 4B:
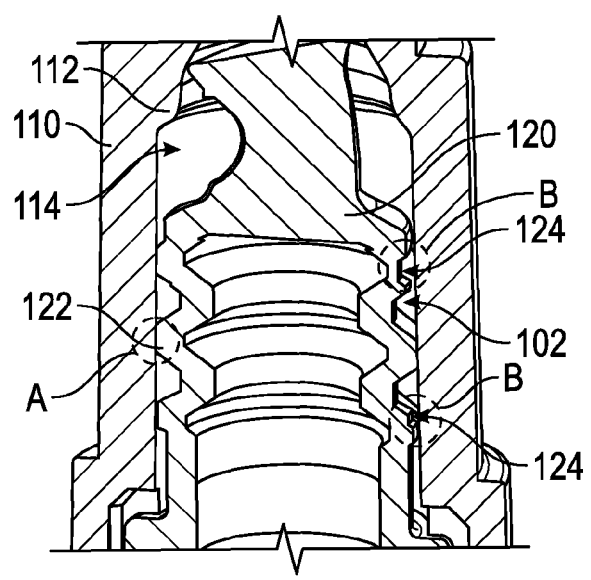

FIGS. 4A-4B are cross-sections of the exemplary valve 100 in an unactuated position according to certain aspects of the present disclosure. FIG. 4A shows the entire connector 100 with a male Luer fitting 40 sealingly mated with the port 116 and displacing the top surface 126 downward, causing the top portion of the collapsible valve 120 to fold around the smiley cut 121 and partially collapsing the bellows 125. As a result of the smiley cut 121 folding, the top surface 126 is canted such that there is a gap between the end of the male Luer fitting 40 such that fluid can enter the connector 100 from the male Luer fitting 40. The cylindrical surfaces of the rings 122 slide along the interior surface 114 and remain in sealing contact with the surface 114.

Figure 5:
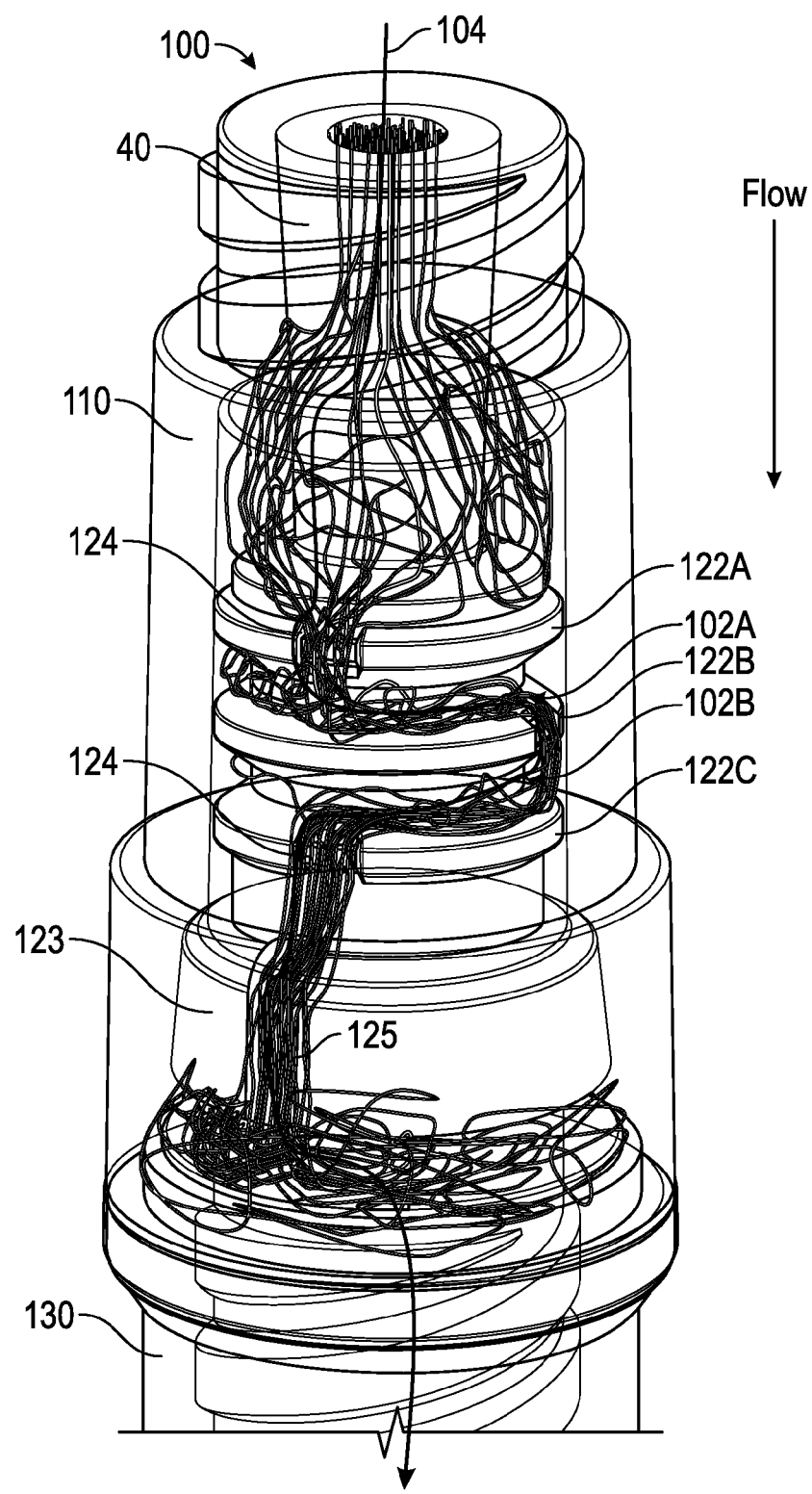
FIG. 5 is a three-dimensional flow diagram of a flow path through the exemplary connector according to certain aspects of the present disclosure.

FIG. 4B is an enlarged view of the portion of FIG. 4A indicated by the dashed-line box labeled "4B." It can be seen on the left side, as viewed in FIG. 4B, of the valve 120 that each of rings 122 are in sealing contact with the interior surface 114, as indicated in the example area indicated by the circle labeled "A." On the right side of collapsible valve 120, it can be seen that the notches 124 provide a flow path past the respective rings 122, as indicated by the circles labeled "B." As each ring 122 has at least one notch 124, with the notches 124 of adjoining rings 122 offset circumferentially from each other, fluid may flow a tortuous path that includes a notch 124 of each ring 122 and a portion of the toroidal flow channel 102 that is formed between pairs of adjacent rings 122 and the interior surface 114, as discussed in greater detail with respect to FIG. 5.

FIG. 5 is a three-dimensional flow diagram of a flow path 104 through the exemplary connector 100 according to certain aspects of the present disclosure. The upper and lower housings 110 and 130 are shown in phantom so as to provide a view of the internal flow paths. FIG. 5 displays a plurality of different flow paths, as calculated by a flow simulation software package, wherein a single example flow path is indicated by the path labeled 104. Fluid enters from the mated male Luer connector 40 and flows past the canted top 126 of the collapsible valve 120 and down to the first ring 122. The fluid travels circumferentially around a portion of the collapsible valve 120 to reach the notch 124 in the first ring 122A and then flows through the notch 124. The fluid then flows circumferentially through the first toroidal flow channel 102A to the notch 124 in the second ring 122B, which is disposed 90° from the notch 124 of the first ring 122A. The fluid flows through the notch 124 and then back through a second toroidal flow channel 102B to a notch in the third ring 122C. The fluid then flows through the notch 124 and down past the base 123 in a channel 125 and out through the base 130.

It can be seen that the disclosed embodiments of the needleless connector 100 provide a tortuous path 104 through the fluid-filled volume within the connector 100 so as to reduce or eliminate portions of the fluid-filled space that are not flushed by the flow of fluid. In certain embodiments, there may be more or fewer notches 124 in each ring 122 and, in certain embodiments, there may be a different number of notches 124 in each ring 122. In certain embodiments, the channel 125 may be offset from the notch 124 in the lowest ring 122 so as to cause additional circumferential flow between the lowest ring 122 and the base 123. In certain embodiments, the notches may be distributed symmetrically about the ring 122 while, in certain other embodiments, the notches may not be distributed evenly.

In summary, the rings and notches of the disclosed needleless connector cooperate to form a tortuous flow path through the connector that reduces the portion of the fluid-filled interior volume that is not flushed by fluid flowing through the connector. By forcing the fluid to flow circumferentially between the rings, the volumes that are not flushed by the linear flow of a conventional valve are coupled to the flow path. Various combinations of rings and notches may be utilized to force this circumferential flow while reducing the pressure drop across the connector.

The previous description is provided to enable any person skilled in the art to practice the various aspects described herein. While the foregoing has described what are considered to be the best mode and/or other examples, it is understood that various modifications to these aspects will be readily apparent to those skilled in the art, and the generic principles defined herein may be applied to other aspects. Thus, the claims are not intended to be limited to the aspects shown herein, but is to be accorded the full scope consistent with the language claims, wherein reference to an element in the singular is not intended to mean "one and only one" unless specifically so stated, but rather "one or more." Unless specifically stated otherwise, the terms "a set" and "some" refer to one or more. Pronouns in the masculine (e.g., his) include the feminine and neuter gender (e.g., her and its) and vice versa. Headings and subheadings, if any, are used for convenience only and do not limit the invention.

To the extent that the terms "include," "have," "with," and the like are used in the description or the claims, such terms are intended to be inclusive in a manner similar to the term "comprise" as "comprise" is interpreted when employed as a transitional word in a claim.

It is understood that the specific order or hierarchy of steps in the processes disclosed is an illustration of exemplary approaches. Based upon design preferences, it is understood that the specific order or hierarchy of steps in the processes may be rearranged. Some of the steps may be performed simultaneously. The accompanying method claims present elements of the various steps in a sample order, and are not meant to be limited to the specific order or hierarchy presented.

Terms such as "top," "bottom," "front," "rear" and the like as used in this disclosure should be understood as referring to an arbitrary frame of reference, rather than to the ordinary gravitational frame of reference. Thus, a top surface, a bottom surface, a front surface, and a rear surface may extend upwardly, downwardly, diagonally, or horizontally in a gravitational frame of reference.

A phrase such as an "aspect" does not imply that such aspect is essential to the subject technology or that such aspect applies to all configurations of the subject technology. A disclosure relating to an aspect may apply to all configurations, or one or more configurations. A phrase such as an aspect may refer to one or more aspects and vice versa. A phrase such as an "embodiment" does not imply that such embodiment is essential to the subject technology or that such embodiment applies to all configurations of the subject technology. A disclosure relating to an embodiment may apply to all embodiments, or one or more embodiments. A phrase such an embodiment may refer to one or more embodiments and vice versa.

The word "exemplary" is used herein to mean "serving as an example or illustration." Any aspect or design described herein as "exemplary" is not necessarily to be construed as preferred or advantageous over other aspects or designs.

All structural and functional equivalents to the elements of the various aspects described throughout this disclosure that are known or later come to be known to those of ordinary skill in the art are expressly incorporated herein by reference and are intended to be encompassed by the claims.

Nothing disclosed herein is intended to be dedicated to the public regardless of whether such disclosure is explicitly recited in the claims. No claim element is to be construed under the provisions of 35 U.S.C. §112, sixth paragraph, unless the element is expressly recited using the phrase "means for" or, in the case of a method claim, the element is recited using the phrase "step for."

What is claimed is:

1. A needleless connector comprising:
a housing having an internal cavity with an interior surface, a port, an output flow channel, and a fluid flow path through the cavity between the port and the output flow channel; and
a collapsible valve disposed within the cavity, the valve comprising:
at least two rings each having a respective surface in sealing contact with the interior surface of the housing; and
one or more notches formed in each of the at least two rings, wherein the one or more notches in a first ring of the at least two rings are circumferentially offset from the one or more notches in a second ring of the at least two rings that is adjacent to the first ring, the one or more notches in at least one of the at least two rings comprise two notches circumferentially disposed 180° from each other,
wherein the fluid flow path passes through one of the one or more notches in each of the at least two rings.

2. The needleless connector of claim 1, wherein the interior surface and the respective surfaces of the at least two rings are cylindrical.

3. The needleless connector of claim 1, further comprising one or more toroidal flow channels formed between adjacent rings of the at least two rings and the interior surface of the housing, wherein the flow path passes through one of the one or more notches in a first ring of the at least two rings, along a portion of a toroidal flow channel that is formed between the first ring, a second ring of the at least two rings that is adjacent to the first ring, and the interior surface of the housing, and then through one of the one or more notches in the second ring.

4. The needleless connector of claim 1, wherein:
a first ring of the at least two rings comprises two notches circumferentially disposed 180° from each other; and
a second ring of the at least two rings is adjacent to the first ring and comprises two notches circumferentially disposed 180° from each other and circumferentially offset from the two notches of the first ring by 90°.

5. The needleless connector of claim 1, wherein the valve further comprises one or more bellows respectively formed under the one or more rings, the bellows configured to partially collapse as the needleless valve moves from an unactuated position to an actuated position while allowing the respective surfaces of the one or more rings to remain in sealing contact with the interior surface.

6. The needleless connector of claim 1, wherein the valve further comprises a smiley cut proximate the port, wherein a portion of the valve folds around the smiley cut when the needleless connector is in an actuated position.

7. The needleless connector of claim 1, wherein:
the valve further comprises a shoulder; and
the housing further comprises a ridge disposed on the interior surface and configured to sealingly contact the shoulder when the needleless connector is in an unactuated position so as to block the fluid flow path.

8. The needleless connector of claim 1, wherein the valve further comprises an unbroken top surface that is flush with the port of the housing when the needleless connector is in an unactuated position.

9. The needleless connector of claim 1, wherein a portion of the housing that is proximate to the port is configured to sealingly mate with a male Luer fitting.

10. A needleless connector comprising:
a housing having an internal cavity with an interior surface, a port, an output flow channel, and a fluid flow path through the cavity between the port and the output flow channel;
a collapsible valve disposed within the cavity, the valve comprising:
at least two rings each having a respective surface in sealing contact with the interior surface of the housing; and one or more notches formed in each of the at least two rings, wherein the one or more notches in a first ring of the at least two rings are circumferentially offset from the one or more notches in a second ring of the at least two rings that is adjacent to the first ring; and one or more toroidal flow channels formed between adjacent rings of the at least two rings and the interior surface of the housing, wherein the flow path passes through one of the one or more notches in a first ring of the at least two rings, along a portion of a toroidal flow channel that is formed between the first ring, a second ring of the at least two rings that is adjacent to the first ring, and the interior surface of the housing, and then through one of the one or more notches in the second ring, wherein the fluid flow path passes through one of the one or more notches in each of the at least two rings.

11. The needleless connector of claim 10, wherein the interior surface and the respective surfaces of the at least two rings are cylindrical.

12. The needleless connector of claim 10, wherein:
a first ring of the at least two rings comprises two notches circumferentially disposed 180° from each other; and
a second ring of the at least two rings is adjacent to the first ring and comprises two notches circumferentially disposed 180° from each other and circumferentially offset from the two notches of the first ring by 90°.

13. The needleless connector of claim 10, wherein the valve further comprises one or more bellows respectively formed under the one or more rings, the bellows configured to partially collapse as the needleless valve moves from an unactuated position to an actuated position while allowing the respective surfaces of the one or more rings to remain in sealing contact with the interior surface.

14. The needleless connector of claim 10, wherein the valve further comprises a smiley cut proximate the port, wherein a portion of the valve fold around the smiley cut when the needleless connector is in an actuated position.

15. The needleless connector of claim 10, wherein:
the valve further comprises a shoulder; and
the housing further comprises a ridge disposed on the interior surface and configured to sealingly contact the shoulder when the needleless connector is in an unactuated position so as to block the fluid flow path.

16. The needleless connector of claim 10, wherein the valve further comprises an unbroken top surface that is flush with the port of the housing when the needleless connector is in an unactuated position.

17. The needleless connector of claim 10, wherein a portion of the housing that is proximate to the port is configured to sealing mate with a male Luer fitting.

* * * * *